United States Patent
Thorwid et al.

(10) Patent No.: US 12,083,540 B2
(45) Date of Patent: Sep. 10, 2024

(54) METHOD FOR SEPARATING CELL CULTURE MIXTURE

(71) Applicant: ALFA LAVAL CORPORATE AB, Lund (SE)

(72) Inventors: Peter Thorwid, Sundbyberg (SE); Kasper Höglund, Rönninge (SE)

(73) Assignee: ALFA LAVAL CORPORATE AB, Lund (SE)

( * ) Notice: Subject to any disclaimer, the term of this patent is extended or adjusted under 35 U.S.C. 154(b) by 706 days.

(21) Appl. No.: 17/296,766

(22) PCT Filed: Dec. 9, 2019

(86) PCT No.: PCT/EP2019/084146
§ 371 (c)(1),
(2) Date: May 25, 2021

(87) PCT Pub. No.: WO2020/120363
PCT Pub. Date: Jun. 18, 2020

(65) Prior Publication Data
US 2022/0023888 A1    Jan. 27, 2022

(30) Foreign Application Priority Data
Dec. 10, 2018 (EP) .................... 18211243

(51) Int. Cl.
*B04B 9/12* (2006.01)
*B04B 1/08* (2006.01)
(Continued)

(52) U.S. Cl.
CPC ............... *B04B 9/12* (2013.01); *B04B 1/08* (2013.01); *B04B 7/14* (2013.01); *B04B 11/02* (2013.01); *C12M 47/02* (2013.01); *C12N 5/0682* (2013.01)

(58) Field of Classification Search
CPC .... B04B 9/12; B04B 1/08; B04B 7/14; B04B 11/02; B04B 7/00; C12M 47/02; C12N 5/0682
See application file for complete search history.

(56) References Cited

U.S. PATENT DOCUMENTS 4,894,050 A      1/1990  Kohlstette et al.
2003/0216237 A1  11/2003 Murayama et al.
(Continued)

FOREIGN PATENT DOCUMENTS

CN        1459337 A      12/2003
CN      104870098 A       8/2015
(Continued)

OTHER PUBLICATIONS

International Search Report, issued in PCT/EP2019/084142, dated Jan. 15, 2020.
(Continued)

*Primary Examiner* — Walter D. Griffin
*Assistant Examiner* — Shuyi S. Liu
(74) *Attorney, Agent, or Firm* — Birch, Stewart, Kolasch & Birch, LLP (57) ABSTRACT

A method for separating a cell culture mixture utilizes a centrifugal separator including a stationary frame, a rotatable assembly and a drive unit for rotating the rotatable assembly relative the frame around a vertical axis of rotation. The rotatable assembly includes a rotor casing enclosing a separation space in which a stack of separation discs is arranged to rotate around an axis of rotation. The rotor casing includes a mechanically hermetically sealed inlet for supply of the cell culture mixture to the separation space and first and second mechanically hermetically sealed liquid outlets. The second mechanically hermetically sealed outlet is arranged at an axial end of the rotor casing and arranged
(Continued)

so that the separated cell phase is discharged at the rotational axis.

20 Claims, 3 Drawing Sheets

(51) Int. Cl.
  B04B 7/14 (2006.01)
  B04B 11/02 (2006.01)
  C12M 1/00 (2006.01)
  C12N 5/071 (2010.01)

(56) References Cited

U.S. PATENT DOCUMENTS

| | | |
|---|---|---|
| 2011/0319248 A1 | 12/2011 | Starbard |
| 2016/0184836 A1 | 6/2016 | Mackel et al. |
| 2017/0189915 A1 | 7/2017 | Mackel et al. |
| 2017/0203306 A1 | 7/2017 | Penkl et al. |
| 2018/0072986 A1 | 3/2018 | Park et al. |

FOREIGN PATENT DOCUMENTS

| | | |
|---|---|---|
| CN | 107838868 A | 1/2016 |
| CN | 108178820 A | 6/2016 |
| EP | 0 241 128 A1 | 10/1987 |
| EP | 2 567 754 A1 | 3/2013 |
| EP | 2 868 210 A1 | 5/2015 |
| WO | WO 2014/000829 A1 | 1/2014 |
| WO | WO 2014/071365 A1 | 5/2014 |
| WO | WO 2015/181175 A2 | 12/2015 |
| WO | WO 2015/181177 A1 | 12/2015 |
| WO | WO 2016/153191 A1 | 9/2016 |
| WO | WO 2016/178100 A1 | 11/2016 |

OTHER PUBLICATIONS

International Search Report, issued in PCT/EP2019/084146, dated Feb. 18, 2020.
Written Opinion (PCT/ISA/237) issued in PCT/EP2019/084142, dated Jan. 15, 2020.
Written Opinion of the International Searching Authority, issued in PCT/EP2019/084146, dated Feb. 18, 2020.
Indian Office Action dated Jun. 9, 2022 for Application No. 202117028941, with an English translation.
Chinese Office Action and Search Report for Chinese Application No. 201980081535.7, dated Jul. 5, 2022. with English translation.
Chinese Office Action and Search Report for Chinese Application No. 201980081606.3, dated Jul. 1, 2022, with English translation.
English translation of Korean Office Action for Korean Application No. 10-2021-7021240, dated Jan. 16, 2023.

METHOD FOR SEPARATING CELL CULTURE MIXTURE

TECHNICAL FIELD

The present inventive concept relates to the field of centrifugal separators. More particularly, it relates to a method for separating a cell culture mixture.

BACKGROUND

Centrifugal separators are generally used for separation of liquids and/or solids from a liquid mixture or a gas mixture. During operation, fluid mixture that is about to be separated is introduced into a rotating bowl and due to the centrifugal forces, heavy particles or denser liquid, such as water, accumulates at the periphery of the rotating bowl whereas less dense liquid accumulates closer to the central axis of rotation. This allows for collection of the separated fractions, e.g. by means of different outlets arranged at the periphery and close to the rotational axis, respectively.

WO 2015/181177 discloses a separator for the centrifugal processing of a pharmaceutical product, such as a fermentation broth. The separator comprises a rotatable outer drum and an exchangeable inner drum arranged in the outer drum. The inner drum comprises means for clarifying the flowable product. The outer drum is driven via drive spindle by a motor arranged below the outer drum. The inner drum extends vertically upwardly through the outer drum which fluid connections arranged at an upper end of the separator.

However, processing a cell culture mixture, such as a cell culture mixture from a fermentation broth, may lead to excessive breakage of the cells, since e.g. mammalian cells and CHO cells may be sensitive to the shear forces experienced within the centrifugal field. This thus leads to a decreased reusability of a separated cell phase. There is thus a need in the art for improved centrifugal separators for separating cell culture mixtures.

SUMMARY

It is an object of the invention to at least partly overcome one or more limitations of the prior art. In particular, it is an object to provide a method for separating a cell culture mixture that decreases the risk of breaking the cells that are being processed in the separator.

As a first aspect of the invention, there is provided a method for separating a cell culture mixture comprising steps of:
a) providing a centrifugal separator comprising a stationary frame, a rotatable assembly and a drive unit for rotating the rotatable assembly relative the frame around an axis of rotation (X), wherein the rotatable assembly comprises a rotor casing enclosing a separation space in which a stack of separation discs is arranged to rotate around a vertical axis (X) of rotation; said rotor casing further comprising a mechanically hermetically sealed inlet for supply of said mammalian cell culture mixture to said separation space; a first mechanically hermetically sealed liquid outlet for discharge of a separated liquid phase, and a second mechanically hermetically sealed liquid outlet for discharge of a separated cell phase; said cell phase having a density that is higher than said liquid phase; wherein said hermetically sealed inlet is arranged at a first axial end of said rotor casing and arranged so that the cell culture mixture to be separated enters said rotor casing at the rotational axis (X); and wherein said second mechanically hermetically sealed outlet is arranged at a second axial end of said rotor casing opposite said first end and arranged so that said separated cell phase is discharged at the rotational axis (X);
b) supplying said cell culture mixture to be separated to said inlet; and
c) discharging a separated cell phase via said second mechanically hermetically sealed liquid outlet and a liquid phase via said first mechanically hermetically sealed liquid outlet.

As an example, the cell culture mixture may comprise shear sensitive cells.

The shear sensitive cells may be selected from Chinese hamster ovary (CHO) cells and mammalian cells.

The stationary frame of the centrifugal separator is a non-rotating part, and the rotatable assembly is supported by the frame, e.g. by means of at least one ball bearing.

The centrifugal separator further comprises a drive member arranged for rotating the rotatable assembly and may comprise an electrical motor or be arranged to rotate the rotatable assembly by suitable transmission, such as a belt or a gear transmission.

The rotatable assembly comprises a rotor casing in which the separation takes place. The rotor casing encloses a separation space in which the separation of the fluid mixture, such as a cell culture mixture, takes place. The rotor casing may be a solid rotor casing and be free of any further outlets for separated phases. Thus, the solid rotor casing may be solid in that it is free of any peripheral ports for discharging e.g. a sludge phase accumulated at the periphery of the separation space. However, in embodiments, the rotor casing comprises peripheral ports for intermittent or continuous discharge of a separated phase from the periphery of the separation space.

The separation space comprises a stack of separation discs arranged centrally around the axis of rotation (X). The stack may comprise frustoconical separation discs.

The separation discs may thus have a frustoconical shape, which refers to a shape having the shape of a frustum of a cone, which is the shape of a cone with the narrow end, or tip, removed. A frustoconical shape has thus an imaginary apex where the tip or apex of the corresponding conical shape is located. The axis of the frustoconical shape is axially aligned with the rotational axis of the solid rotor casing. The axis of the frustoconical portion is the direction of the height of the corresponding conical shape or the direction of the axis passing through the apex of the corresponding conical shape.

The separation discs may alternatively be axial discs arranged around the axis of rotation.

The separation discs may e.g. comprise a metal or be of metal material, such as stainless steel. The separation discs may further comprise a plastic material or be of a plastic material.

The mechanically hermetically sealed inlet is for receiving the fluid to be separated and to guide the fluid to the separation space, a first mechanically hermetically sealed liquid outlet for discharge of a separated liquid phase and a second mechanically hermetically sealed liquid outlet for discharge of a separated cell phase.

The inlet is arranged at a first axial end, such as the lower axial end, of the rotor casing whereas the second mechanically hermetically sealed liquid outlet is arranged at the opposite axial end, such as the upper axial end, of the rotor. The first mechanically hermetically sealed liquid outlet for discharge of a separated liquid phase may be arranged at the lower axial end or at the upper axial end of the rotor casing.

A mechanical hermetic seal refers to a seal that is supposed to give rise to an airtight seal between a stationary portion and the rotor casing and prevent air from outside the rotor casing to contaminate the feed. Therefore, the rotor casing may be arranged to be completely filled with liquid, such as cell culture mixture, during operation. This means that no air or free liquid surfaces is meant to be present in the rotor casing during operation.

Thus, as used herein, a mechanically hermetic seal is a fully hermetic seal, as compared to a semi-hermetic seal or a hydro-hermetic seal.

The first aspect of the invention is based on the insight that for separation of shear sensitive liquid, such as a cell culture mixture, it is an advantage if the cells can enter and leave the rotating parts of the separator at the radial centre, i.e. at the rotational axis (X). This imparts less rotational energy for the separated cells that leaves the separator and thus decreases the risk of cell breakage. The cells are thus discharged from the rotor casing, and from the rotatable assembly, at rotational axis (X).

A phase being discharged or supplied "at the rotational axis" comprises the phase being discharged or supplied within a certain diameter that comprises the rotational axis.

In embodiments of the first aspect of the invention, the mechanically hermetically sealed outlets are free of any means for adding pressure for discharging the separated liquid phase and the separated cell phase.

A means for adding or boosting pressure may be a pump wheel or any centripetal pump, such as a paring disc commonly used within the field of centrifugal separators. Having outlets that are free of any means for adding or boosting pressure further reduces the risk of cell breakage when discharging the separated cell phase from the centrifugal separator.

In embodiments of the first aspect of the invention, the rotor casing further comprises at least one outlet conduit for transporting the separated cell phase from the separation space to the second mechanically hermetically sealed liquid outlet, said conduit extending from a radially outer position of said separation space to said second mechanically hermetically sealed liquid outlet.

There may thus be at least one outlet conduit arranged for transporting the separated cell phase from the separation space to the second mechanically hermetically sealed liquid outlet. The at least one conduit extends from a radially outer position in the separation space to the heavy phase outlet, which is thus at a radially inner position.

As an example, the conduit inlet may be arranged at the radially outer position and a conduit outlet at a radially inner position. Further, the at least one outlet conduit may be arranged with an upward tilt from the conduit inlet to the conduit outlet.

Thus, relative the radial plane, the conduit may be tilted axially upwards from the conduit inlet in the separation space to the conduit outlet at the heavy phase outlet. This may facilitate transport of the separated cell phase in the conduit.

The conduit inlet may be arranged at an axially upper position in the separation space. The conduit inlet may be arranged at an axial position where the separation space has it largest inner diameter.

The outlet conduit may be a pipe. As an example, the rotor casing may comprise a single outlet conduit. In other examples, the rotor casing, such as in an insert (see below) may comprise at least two such outlet conduits, such as at least three, such as at least five, outlet conduits.

As an example, the at least one outlet conduit is tilted with an upward tilt of at least 2 degrees relative the radial plane. As an example, the at least one outlet conduit may be tilted with an upward tilt of at least 5 degrees, such as at least 10 degrees, relative the radial plane.

The at least one outlet conduit may facilitate transport of the separated heavy phase in the separation space to the heavy phase outlet.

In embodiments of the first aspect of the invention, the centrifugal separator further comprises a first rotatable seal for sealing and connecting said inlet to a stationary inlet conduit, wherein at least a part of said stationary inlet conduit is arranged around the rotational axis (X). Thus, the stationary inlet conduit may be in alignment with the rotational axis.

The first rotatable seal may thus be a mechanical hermetic seal, which is a rotatable seal for connecting and sealing the inlet to a stationary inlet conduit. The first rotatable seal may be arranged at the border of the rotor casing and stationary portion of the frame and may thus comprise a stationary part and a rotatable part.

The stationary inlet conduit may thus also be part of the stationary frame and is arranged at the rotational axis (X).

The first rotatable seal may be a double seal that also seals the first mechanically hermetically sealed liquid outlet for discharging the separated liquid phase.

In embodiments of the first aspect of the invention, the centrifugal separator further comprises a second rotatable seal for sealing and connecting said second mechanically hermetically sealed liquid outlet to a stationary outlet conduit arranged around the rotational axis (X). Thus, the stationary outlet conduit may be in alignment with the rotational axis.

In analogy, the second rotatable seal may also be a mechanical hermetic seal, which is a rotatable seal for connecting and sealing the outlet to a stationary outlet conduit. The second rotatable seal may be arranged at the border of the rotor casing and stationary portion of the frame and may thus comprise a stationary part and a rotatable part.

The stationary outlet conduit may thus also be part of the stationary frame and is arranged at the rotational axis (X).

In embodiments of the first aspect of the invention, the rotatable assembly comprises an exchangeable separation insert and a rotatable member; said insert comprising said rotor casing and being supported by said rotatable member.

The exchangeable separation insert may thus be a pre-assembled insert being mounted into the rotatable member, which may function as a rotatable support for the insert. The exchangeable insert may thus easily be inserted and disengaged from the rotatable member as a single unit.

According to embodiments, the exchangeable separation insert is a single use separation insert. Thus, the insert may be adapted for single use and be a disposable insert. The exchangeable insert may thus be for processing of one product batch, such as a single product batch in the pharmaceutical industry, and then be disposed.

The exchangeable separation insert may comprise a polymeric material or consist of a polymeric material. As an example, the rotor casing and the stack of separation discs may comprise, or be of a polymeric material, such as polypropylene, platinum cured silicone or BPA free polycarbonate. The polymer parts of the insert may be injection moulded. However, the exchangeable separation insert may also comprise metal parts, such as stainless steel. For example, the stack of separation discs may comprise discs of stainless steel.

The exchangeable insert may be a sealed sterile unit.

Further, if the rotor casing comprises an exchangeable separation insert, the rotor casing may be arranged to be solely externally supported by external bearings.

Furthermore, the exchangeable separation insert, and the rotatable member, may be free of any rotatable shaft that is arranged to be supported by external bearings.

As an example, the outer surface of the exchangeable insert may be engaged within a supporting surface of the rotatable member, thereby supporting said exchangeable insert within said rotatable member.

Consequently, the centrifugal separator may be a modular centrifugal separator or comprising a base unit and the rotatable assembly comprising an exchangeable separation insert. The base unit may comprise a stationary frame and a drive unit for rotating the rotatable assembly about the axis of rotation. The rotatable assembly may have a first axial end and a second axial end, and may delimit an inner space at least in a radial direction, the inner space being configured for receiving at least one part of the exchangeable separation insert therein. The rotatable assembly may be provided with a first through opening to the inner space at the first axial end and configured for a first fluid connection of the exchangeable separation insert to extend through the first through opening. The rotatable assembly may also comprise a second through opening to the inner space at the second axial end and configured for a second fluid connection of the exchangeable separation insert to extend through the second through opening.

However, in embodiments of the first aspect of the invention, the rotatable assembly further comprises a spindle arranged to rotate coaxially with said rotor casing and wherein said spindle is rotatably supported by the stationary frame via at least one bearing.

Thus, the rotor casing may be arranged at an end of a rotatable spindle, and this spindle may be supported in the frame by at least one bearing device, such as by at least one ball-bearing.

As an example, said spindle may comprise a central duct arranged around the axis of rotation (X) and in fluid connection with said inlet, and wherein said first rotatable seal is sealing and connecting said central duct to said stationary inlet conduit.

Thus, the spindle may be a hollow spindle and may be used for supplying feed to the inlet. The spindle may further comprise an outer annular duct for discharging a separated liquid phase, such as the separated liquid light phase.

The above discussions of the first aspect, examples and embodiments, relate to the centrifugal separator provided in the step a) of the method.

As a further aspect there may be provided a system for separating a cell culture mixture, comprising
  a centrifugal separator according to aspects and/or embodiments discussed herein;
  a fermenter for hosting a cell culture mixture;
  a connection from the bottom of the fermenter to the centrifugal separator arranged so that the cell culture mixture to be separated is supplied to the inlet at the axially lower end of the centrifugal separator.

The method of the first aspect may be performed in a system of the further aspect.

The fermenter may be a fermenter tank.

The connection may be any suitable connection, such as a pipe or a tube. The connection may be a direct connection between the fermenter and the centrifugal separator.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings, like reference numerals will be used for like elements unless stated otherwise.

DETAILED DESCRIPTION

In the above the inventive concept has mainly been described with reference to a limited number of examples. However, as is readily appreciated by a person skilled in the art, other examples than the ones disclosed above are equally possible within the scope of the inventive concept, as defined by the appended claims.

A method 50 for separating a cell culture mixture, as discussed below with reference to FIG. 6, may utilise a centrifugal separator as discussed below with reference to FIGS. 1-4.

Figure 1:
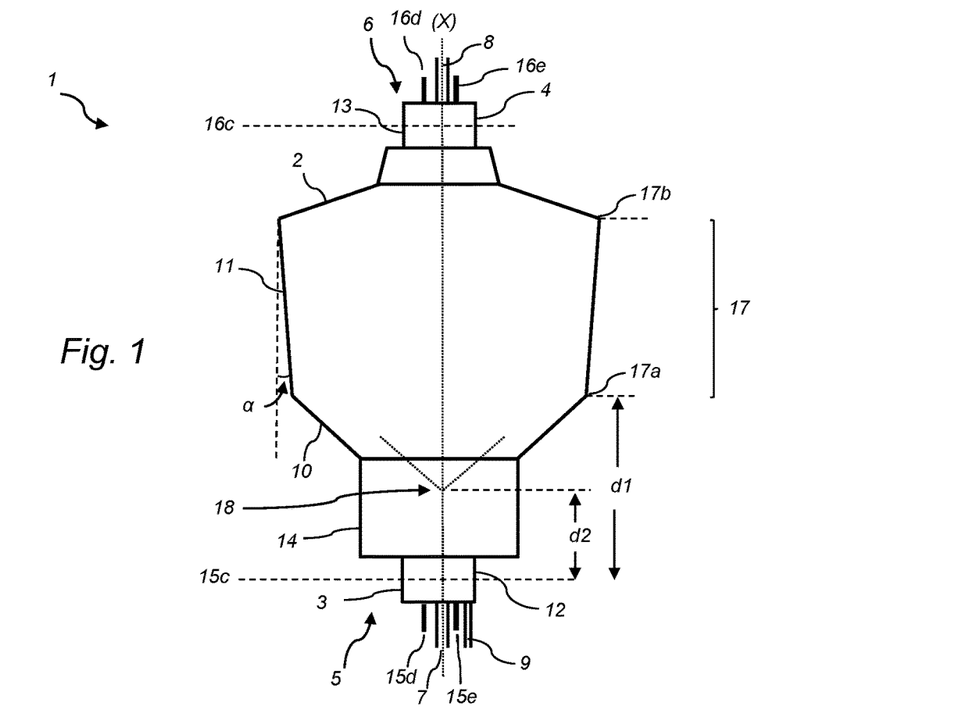
FIG. 1 is a schematic outer side view of a rotor casing forming an exchangeable separation insert for a centrifugal separator for separating a cell culture mixture.

FIG. 1 shows an outer side view of a rotatable member in the form of an exchangeable separation insert 1 that may be used in a centrifugal separator of the present disclosure.

The insert 1 comprises a rotor casing 2 arranged between a first, lower stationary portion 3 and a second, upper stationary portion 4, as seen in the axial direction defined by rotational axis (X). The first stationary portion 3 is at the lower axial end 5 of the insert 1, whereas the second stationary portion 4 is arranged at the upper axial end 6 of the insert 1.

The feed inlet is in this example arranged at the axial lower end 5, and the feed is supplied via a stationary inlet conduit 7 arranged in the first stationary portion 3. The stationary inlet conduit 7 is arranged at the rotational axis (X). The first stationary portion 3 further comprises a stationary outlet conduit 9 for the separated liquid phase of lower density, also called the separated liquid light phase.

There is further a stationary outlet conduit 8 arranged in the upper stationary portion 4 for discharge of the separated phase of higher density, also called the liquid heavy phase. Thus, in this embodiment, the feed is supplied via the lower axial end 5, the separated light phase is discharged via the lower axial end 5, whereas the separated heavy phase is discharged via the upper axial end 6.

The outer surface of the rotor casing 2 comprises a first 10 and second 11 frustoconical portion. The first frustoconical portion 10 is arranged axially below the second frustoconical portion 11. The outer surface is arranged such that the imaginary apex of the first 10 and second 11 frustoconical portions both point in the same axial direction along the rotational axis (X), which in this case is axially down towards the lower axial end 5 of the insert 1.

Furthermore, the first frustoconical portion 10 has an opening angle that is larger than the opening angle of the second frustoconical portion 11. The opening angle of the first frustoconical portion may be substantially the same as the opening angle of a stack of separation discs contained within the separation space 17 of the rotor casing 2. The opening angle of the second frustoconical portion 11 may be smaller than the opening angle of a stack of separation discs contained within the separation space of the rotor casing 2. As an example, the opening angle of the second frustoconical portion 11 may be such that the outer surface forms an angle $\alpha$ with rotational axis that is less than 10 degrees, such as less than 5 degrees. The rotor casing 2 having the two frustoconical portions 10 and 11 with imaginary apexes pointing downwards allows for the insert 1 to be inserted into a rotatable member 30 from above. Thus, the shape of the outer surface increases the compatibility with an external rotatable member 30, which may engage the whole, or part of the outer surface of the rotor casing 2, such as engage the first 10 and second 11 frustoconical portions.

There is a lower rotatable seal arranged within lower seal housing 12 which separates the rotor casing 2 from the first stationary portion 3 and an upper rotatable seal arranged within upper seal housing 13 which separates the rotor casing 2 from the second stationary portion 4. The axial position of the sealing interface within the lower seal housing 12 is denoted 15c, and the axial position of the sealing interface within the upper seal housing 13 is denoted 16c. Thus, the sealing interfaces formed between such stationary part 15a, 16a and rotatable part 15b, 16b of the first 15 and second 16 rotatable seals also form the interfaces or border between the rotor casing 2 and the first 15 and second 16 stationary portions of the insert 1.

There are further a seal fluid inlet 15d and a seal fluid outlet 15e for supplying and withdrawing a seal fluid, such as a cooling liquid, to the first rotatable seal 15 and in analogy, a seal fluid inlet 16d and a seal fluid outlet 16e for supplying and withdrawing a seal fluid, such as a cooling liquid, to the second rotatable seal 16.

Shown in FIG. 1 is also the axial positions of the separation space 17 enclosed within the rotor casing 2. In this embodiment, the separation space is substantially positioned within the second frustoconical portion 11 of the rotor casing 2. The heavy phase collection space (17c) of the separation space 17 extends from a first, lower, axial position 17a to a second, upper, axial position 17b. The inner peripheral surface of the separation space 17 may form an angle with the rotational axis (X) that is substantially the same as angle $\alpha$, i.e. the angle between the outer surface of the second frustoconical portion 11 and the rotational axis (X). The inner diameter of the separation space 17 may thus increase continuously from the first axial position 17a to the second axial position 17b. Angle $\alpha$ may be less than 10 degrees, such as less than 5 degrees.

The exchangeable separation insert 1 has a compact form that increases the manoeuvrability and handling of the insert 1 by an operator. As an example, the axial distance between the separation space 17 and the first stationary portion 3 at the lower axial end 5 of the insert may be less than 20 cm, such as less than 15 cm. This distance is denoted d1 in FIG. 1, and is in this embodiment the distance from the lowest axial position 17a of the heavy phase collection space (17c) of the separation space 17 to the sealing interface 15c of the first rotatable seal 15. As a further example, if the separation space 17 comprises a stack of frustoconical separation discs, the frustoconical separation disc that is axially lowest in the stack and closest to the first stationary portion 3, may be arranged with the imaginary apex 18 positioned at an axial distance d2 from the first stationary portion 3 that is less than 10 cm, such as less than 5 cm. Distance d2 is in this embodiment the distance from the imaginary apex 18 of the axially lowermost separation disc to the sealing interface of the first rotatable seal 15.

Figure 2:
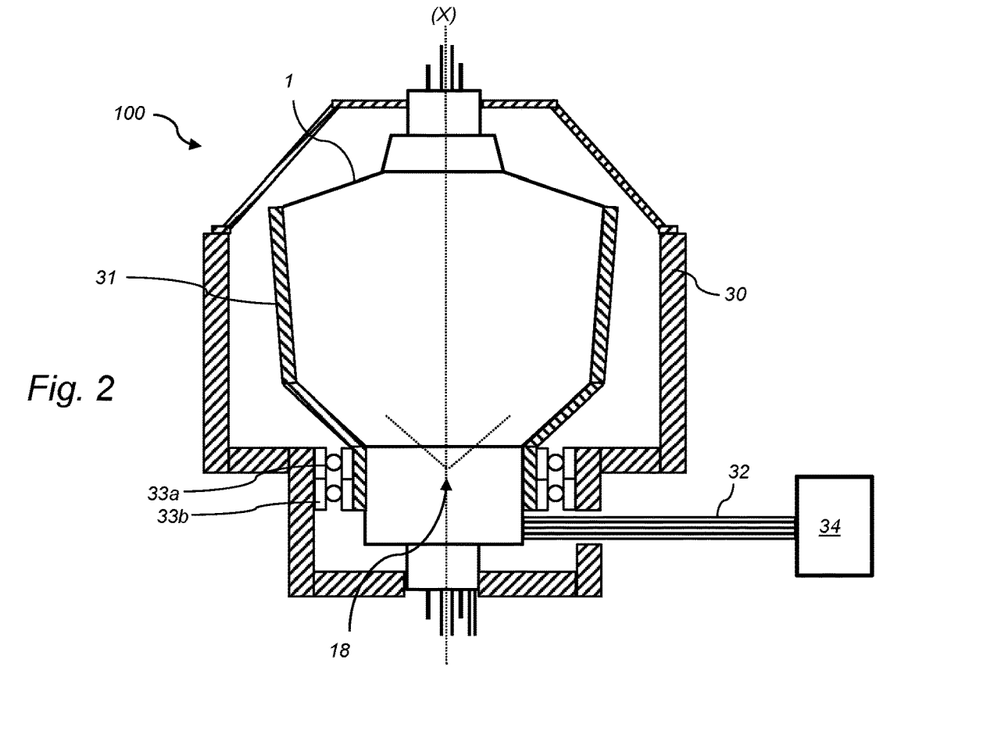
FIG. 2 is a schematic section of a centrifugal separator comprising an exchangeable insert as shown in FIG. 1.

FIG. 2 shows a schematic drawing of the exchangeable separation insert 1 being inserted within centrifugal separator 100, which comprises a stationary frame 30 and a rotatable member 31 that is supported by the frame by means of supporting means in the form of an upper and lower ball bearing 33a, 33b. There is also a drive unit 34, which in this case is arranged for rotating the rotatable member 31 around the axis of rotation 31 via drive belt 32. However, other driving means are possible, such as an electrical direct drive.

The exchangeable separation insert 1 is inserted and secured within rotatable member 31. The rotatable member 31 thus comprises an inner surface for engaging with the outer surface of the rotor casing 2. The upper and lower ball bearings 33a, 33b are both positioned axially below the separation space 17 within the rotor casing 2 such that the cylindrical portion 14 of the outer surface of the rotor casing 2 is positioned axially at the bearing planes. The cylindrical portion 14 thus facilitates mounting of the insert within at least one large ball bearing. The upper and lower ball bearings 33a, 33b may have an inner diameter of at least 80 mm, such as at least 120 mm.

Further, as seen in FIG. 2, the insert 1 is positioned within rotatable member 31 such that the imaginary apex 18 of the lowermost separation disc is positioned axially at or below at least one bearing plane of the upper and lower ball bearings 33a, 33b.

Moreover, the separation insert is mounted within the separator 1 such that the axial lower part 5 of the insert 1 is positioned axially below the supporting means, i.e. the upper and lower bearings 33a, 33b. The rotor casing 2 is in this example arranged to be solely externally supported by the rotatable member 31.

The separation insert 1 is further mounted within the separator 100 to allow easy access to the inlet and outlets at the top and bottom of the insert 1.

Figure 3:
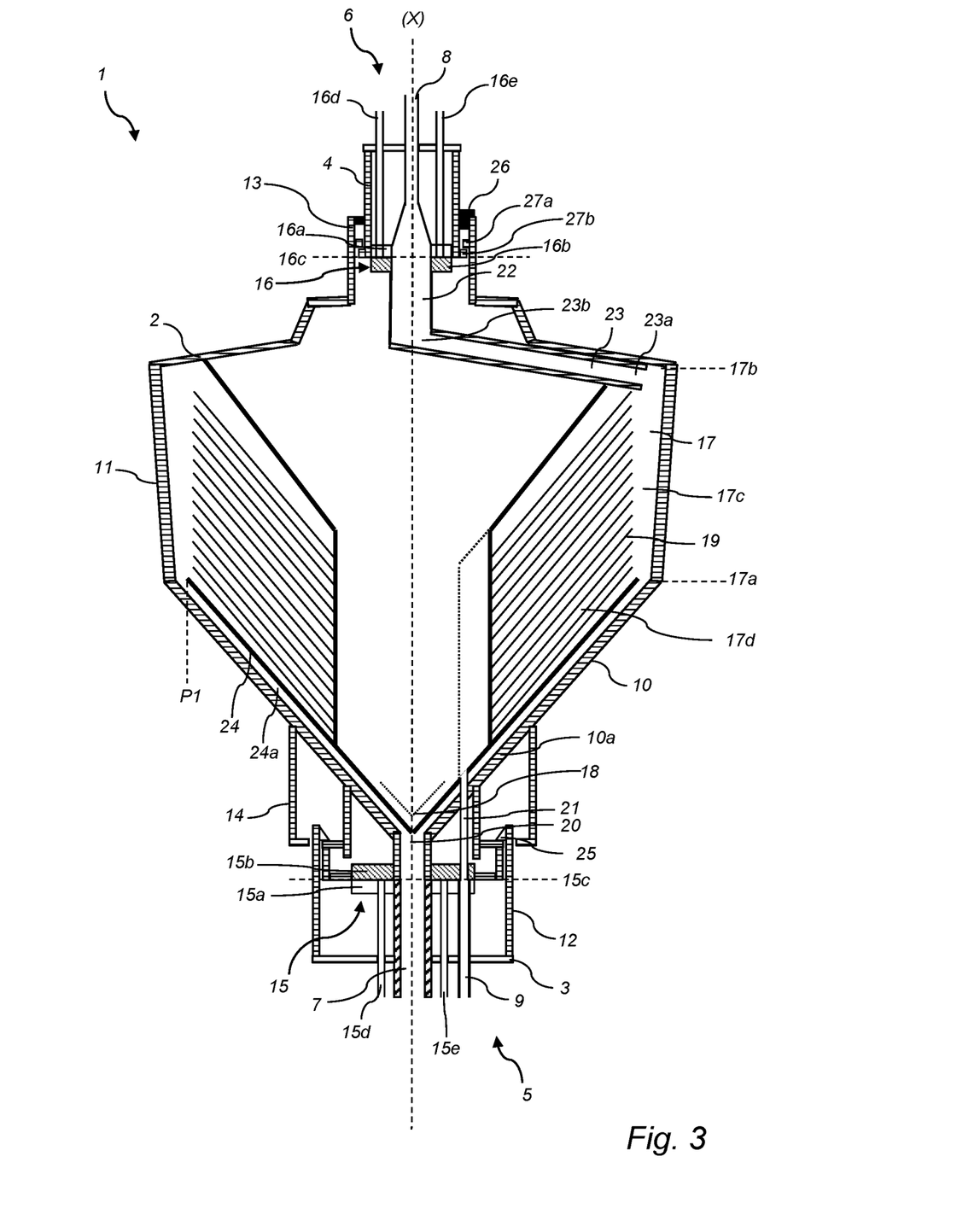
FIG. 3 is a schematic section view of the exchangeable separation insert as shown in FIG. 1.

FIG. 3 shows a schematic illustration of cross-section of an embodiment of exchangeable separation insert 1 of the present disclosure. The insert 1 comprises a rotor casing arranged to rotate around rotational axis (X) and arranged between a first, lower stationary portion 3 and a second, upper stationary portion 4. The first stationary portion 3 is thus arranged at the lower axial end 5 of the insert, whereas the second stationary portion 4 is arranged at the upper axial end 6 of the insert 1.

The feed inlet 20 is in this example arranged at the axial lower end 5, and the feed is supplied via a stationary inlet conduit 7 arranged in the first stationary portion 3. The stationary inlet conduit 7 may comprise a tubing, such as a plastic tubing. The stationary inlet conduit 7 is arranged at the rotational axis (X) so that the material to be separated is supplied at the rotational centre. The feed inlet 20 is for receiving the fluid mixture to be separated.

The feed inlet 20 is in this embodiment arranged at the apex of an inlet cone 10a, which on the outside of the insert 1 also forms the first frustoconical outer surface 10. There is further a distributor 24 arranged in the feed inlet for distributing the fluid mixture from the inlet 24 to the separation space 17.

The separation space 17 comprises an outer heavy phase collection space 17c that extends axially from a first, lower axial position 17a to a second, upper axial position 17b. The separation space further comprises a radially inner space formed by the interspaces between the separation discs of the stack 19.

The distributor 24 has in this embodiment a conical outer surface with the apex at the rotational axis (X) and pointing toward the lower end 5 of the insert 1. The outer surface of the distributor 24 has the same conical angle as the inlet cone 10a. There is further a plurality of distributing channels 24a extending along the outer surface for guiding the fluid mixture to be separated continuously axially upwards from an axially lower position at the inlet to an axially upper position in the separation space 17. This axially upper position is substantially the same as the first, lower axial position 17a of the heavy phase collection space 17c of the separation space 17. The distribution channels 24a may for example have a straight shape or a curved shape, and thus extend between the outer surface of the distributor 24 and the inlet cone 24a. The distribution channels 24 may be diverging from an axially lower position to an axially upper position. Furthermore, the distribution channels 24 may be in the form of tubes extending from an axially lower position to an axially upper position.

There is further a stack 19 of frustoconical separation discs arranged coaxially in the separation space 17. The separation discs in the stack 19 are arranged with the imaginary apex pointing to the axially lower end 5 of the separation insert, i.e. towards the inlet 20. The imaginary apex 18 of the lowermost separation disc in the stack 19 may be arranged at a distance that is less than 10 cm from the first stationary portion 3 in the axial lower end 5 of the insert 1. The stack 19 may comprise at least 20 separation discs, such as at least 40 separation discs, such as at least 50 separation discs, such as at least 100 separation discs, such as at least 150 separation discs. For clarity reasons, only a few discs are shown in FIG. 1. In this example, the stack 19 of separation discs is arranged on top of the distributor 24, and the conical outer surface of the distributor 24 may thus have the same angle relative the rotational axis (X) as the conical portion of the frustoconical separation discs. The conical shape of the distributor 24 has a diameter that is about the same or larger than the outer diameter of the separation discs in the stack 19. Thus, the distribution channels 24a may thus be arranged to guide the fluid mixture to be separated to an axial position 17a in the separation space 17 that is at a radial position $P_1$ that is outside the radial position of the outer circumference of the frustoconical separation discs in the stack 19.

The heavy phase collection space 17c of the separation space 17 has in this embodiment an inner diameter that continuously increases from the first, lower axial position 17a to the second, upper axial position 17b. There is further an outlet conduit 23 for transporting a separated heavy phase from the separation space 17. This conduit 23 extends from a radially outer position of the separation space 17 to the heavy phase outlet 22. In this example, the conduit is in the form of a single pipe extending from a central position radially out into the separation space 17. However, there may be at least two such outlet conduits 23, such as at least three, such as at least five, outlet conduits 23. The outlet conduit 23 has thus a conduit inlet 23a arranged at the radially outer position and a conduit outlet 23b at a radially inner position, and the outlet conduit 23 is arranged with an upward tilt from the conduit inlet 23a to the conduit outlet 23b. As an example, the outlet conduit may be tilted with an upward tilt of at least 2 degrees, such as at least five degrees, such as at least ten degrees, relative the radial plane.

The outlet conduit 23 is arranged at an axially upper position in the separation space 17, such that the outlet conduit inlet 23a is arranged for transporting separated heavy phase from the axially uppermost position 17b of the separation space 17. The outlet conduit 23 further extends radially out into the separation space 17 so that outlet conduit inlet 23a is arranged for transporting separated heavy phase from the periphery of the separation space 17, i.e. from the radially outermost position in the separation space at the inner surface of the separation space 17.

The conduit outlet 23b of the stationary outlet conduit 23 ends at the heavy phase outlet 22, which is connected to a stationary outlet conduit 8 arranged in the second, upper stationary portion 4. Separated heavy phase is thus discharged via the top, i.e. at the upper axial end 6, of the separation insert 1.

Furthermore, separated liquid light phase, which has passed radially inwards in the separation space 17 through the stack of separation discs 19, is collected in the liquid light phase outlet 21 arranged at the axially lower end of the rotor casing 2. The liquid light phase outlet 21 is connected to a stationary outlet conduit 9 arranged in the first, lower stationary portion 3 of the insert 1. Thus, separated liquid light phase is discharged via the first, lower, axial end 5 of the exchangeable separation insert 1.

The stationary outlet conduit 9 arranged in the first stationary portion 3 and the stationary heavy phase conduit 8 arranged in the second stationary portion 4 may comprise tubing, such as plastic tubing.

There is further a lower rotatable seal 15, which separates the rotor casing 2 from the first stationary portion 3, arranged within lower seal housing 12 and an upper rotatable seal, which separates the rotor casing from the second stationary portion 4, arranged within upper seal housing 13. The first 15 and second 16 rotatable seals are hermetic seals, thus forming mechanically hermetically sealed inlet and outlets.

The lower rotatable seal 15 may be attached directly to the inlet cone 10a without any additional inlet pipe, i.e. the inlet may be formed at the apex of the inlet cone directly axially above the lower rotatable seal 15. Such an arrangement enables a firm attachment of the lower mechanical seal at a large diameter to minimize axial run-out.

The lower rotatable seal 15 seals and connects both the inlet 20 to the stationary inlet conduit 7 and seals and connects the liquid light phase outlet 21 to the stationary liquid light phase conduit 9. The lower rotatable 15 seal thus forms a concentric double mechanical seal, which allows for easy assembly with few parts. The lower rotatable seal 15 comprises a stationary part 15a arranged in the first stationary portion 3 of the insert 1 and a rotatable part 15b arranged in the axially lower portion of the rotor casing 2. The rotatable part 15b is in this embodiment a rotatable sealing ring arranged in the rotor casing 2 and the stationary part 15a is a stationary sealing ring arranged in the first stationary portion 3 of the insert 1. There are further means (not shown), such as at least one spring, for bringing the rotatable sealing ring and the stationary sealing ring into engagement with each other, thereby forming at least one sealing interface 15c between the rings. The formed sealing interface extends substantially in parallel with the radial plane with respect to the axis of rotation (X). This sealing interface 15c thus forms the border or interface between the rotor casing 2 and the first stationary portion 3 of the insert 1. There are further connections 15d and 15e arranged in the first stationary portion 3 for supplying a liquid, such as a cooling liquid, buffer liquid or barrier liquid, to the lower rotatable seal 15. This liquid may be supplied to the interface 15c between the sealing rings.

In analogy, the upper rotatable seal 16 seals and connects the heavy phase outlet 22 to the stationary outlet conduit 8. The upper mechanical seal may also be a concentric double mechanical seal. The upper rotatable seal 16 comprises a stationary part 16a arranged in the second stationary portion 4 of the insert 1 and a rotatable part 16b arranged in the axially upper portion of the rotor casing 2. The rotatable part 16b is in this embodiment a rotatable sealing ring arranged in the rotor casing 2 and the stationary part 16a is a stationary sealing ring arranged in the second stationary portion 4 of the insert 1. There are further means (not shown), such as at least one spring, for bringing the rotatable sealing ring and the stationary sealing ring into engagement with each other, thereby forming at least one sealing interface 16c between the rings. The formed sealing interface 16c extends substantially in parallel with the radial plane with respect to the axis of rotation (X). This sealing interface 16c thus forms the border or interface between the rotor casing 2 and the second stationary portion 4 of the insert 1. There are further connections 16d and 16e arranged in the second stationary portion 4 for supplying a liquid, such as a cooling liquid, buffer liquid or barrier liquid, to the upper rotatable seal 16. This liquid may be supplied to the interface 16c between the sealing rings.

Furthermore, FIG. 3 shows the exchangeable separation insert in a transport mode. In order to secure the first stationary portion 3 to the rotor casing 2 during transport, there is a lower securing means 25 in the form of a snap fit that axially secures the lower rotatable seal 15 to the cylindrical portion 14 of rotor casing 2. Upon mounting the exchangeable insert 1 in a rotating assembly, the snap fit 25 may be released such that the rotor casing 2 becomes rotatable around axis (X) at the lower rotatable seal.

Moreover, during transport, there is an upper securing means 27a,b that secures the position of the second stationary portion 4 relative the rotor casing 2. The upper securing means is in the form of an engagement member 27a arranged on the rotor casing 2 that engages with an engagement member 27b on the second stationary portion 4, thereby securing the axial position of the second stationary portion 4. Further, there is a sleeve member 26 arranged in a transport or setup position in sealing abutment with the rotor casing 2 and the second stationary portion 4. The sleeve member 26 is further resilient and may be in the form of a rubber sleeve. The sleeve member is removable from the transport or setup position for permitting the rotor casing 2 to rotate in relation to the second stationary portion 4. Thus, the sleeve member 26 seals radially against the rotor casing 2 and radially against the second stationary portion 4 in the setup or transport position. Upon mounting the exchangeable insert 1 in a rotating assembly, the sleeve member may be removed and an axial space between engagement members 27a and 27b may be created in order to allow rotation of the rotor casing 2 relative the second stationary portion 4.

The lower and upper rotatable seals 15, 16 are mechanical seals, hermetically sealing the inlet and the two outlets.

During operation, the exchangeable separation insert 1, inserted into a rotatable member 31, is brought into rotation around rotational axis (X). Liquid mixture to be separated is supplied via stationary inlet conduit 7 to the inlet 20 of the insert, and is then guided by the guiding channels 24 of the distributor 24 to the separation space 17. Thus, the liquid mixture to be separated is guided solely along an upwards path from the inlet conduit 7 to the separation space 17. Due to a density difference the liquid mixture is separated into a liquid light phase and a liquid heavy phase. This separation is facilitated by the interspaces between the separation discs of the stack 19 fitted in the separation space 17. The separated liquid heavy phase is collected from the periphery of the separation space 17 by outlet conduit 22 and is forced out via the heavy phase outlet 22 arranged at the rotational axis (X) to the stationary heavy phase outlet conduit 8. Separated liquid light phase is forced radially inwards through the stack 19 of separation discs and led via the liquid light phase outlet 21 out to the stationary light phase conduit 9.

Consequently, in this embodiment, the feed is supplied via the lower axial end 5, the separated light phase is discharged via the lower axial end 5, whereas the separated heavy phase is discharged via the upper axial end 6.

Further, due to the arrangement of the inlet 20, distributor 24, stack 19 of separation discs and the outlet conduit 23 as disclosed above, the exchangeable separation insert 1 is de-aerated automatically, i.e. the presence of air-pockets is eliminated or decreased so that any air present within the rotor casing is forced to travel unhindered upwards and out via the heavy phase outlet. Thus, at stand-still, there are no air pockets, and if the insert 1 is filled up through the feed inlet all air may be vented out through the heavy phase outlet 22. This also facilitates filling the separation insert 1 at standstill and start rotating the rotor casing when liquid mixture to be separated or buffer fluid for the liquid mixture is present within the insert 1.

As also seen in FIG. 3, the exchangeable separation insert 1 has a compact design. As an example, the axial distance between the imaginary apex 18 of the lowermost separation disc in the stack 19 may be less than 10 cm, such as less than 5 cm, from the first stationary portion 3, i.e. less than 10 cm, such as less than 5 cm, from the sealing interface 15c of the lower rotatable seal 15.

Further, the rotatable part of the first rotatable seal may be arranged directly onto the axially lower portion of the rotor casing.

Figures 4, 5, 6:
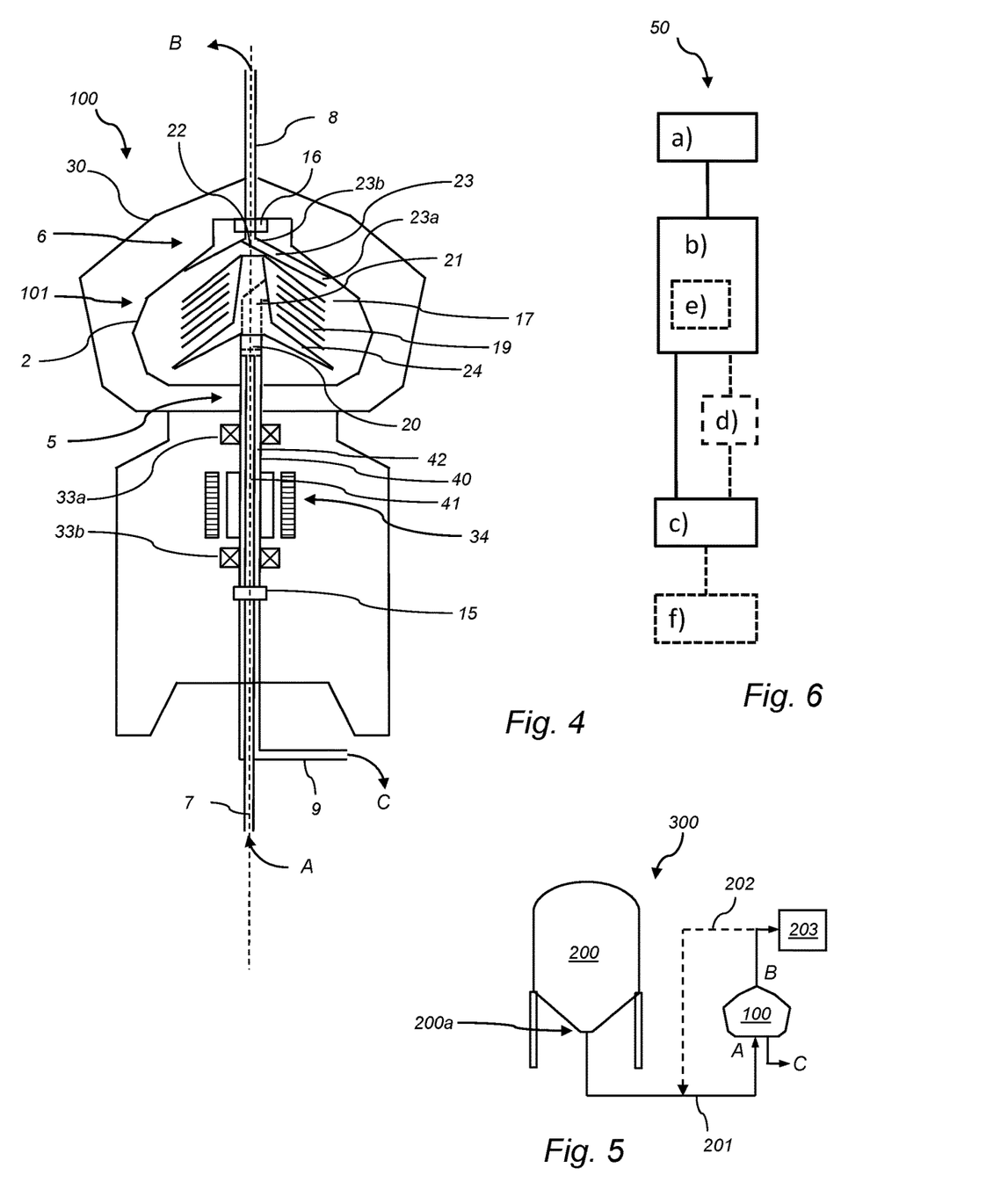
FIG. 4. is a schematic illustration of a centrifugal separator for separation of a cell culture mixture.
FIG. 5. is a schematic illustration of a system for separating a cell culture mixture.
FIG. 6 shows a method for separating a cell culture mixture.

FIG. 4 shows a centrifugal separator 100 for separating a cell culture mixture. The separator 100 comprises a frame 30, a hollow spindle 40, which is rotatably supported by the frame 30 in a bottom bearing 33b and a top bearing 33a, and a rotatable member 1 having a rotor casing 2. The rotor casing 2 is adjoined to the axially upper end of the spindle 40 to rotate together with the spindle 40 around the axis (X) of rotation. The rotor casing 2 encloses a separation space 17 in which a stack 19 of separation discs is arranged in order to achieve effective separation of a cell culture mixture that is processed. The separation discs of the stack 19 have a frustoconical shape with the imaginary apex pointing axially upwards and are examples of separation surface enlarging inserts. The stack 19 is fitted centrally and coaxially with the rotor casing 2. In FIG. 4, only a few separation discs are shown. The stack 19 may for example contain above 100 separation discs, such as above 200 separation discs.

The rotor casing 2 has a mechanically hermetically sealed liquid outlet 21 for discharge of a separated liquid light phase, and a heavy phase outlet 22 for discharge of a cell phase of higher density than the separated liquid light phase. The liquid light phase may thus contain an extracellular biomolecule that has been expressed by the cells during fermentation.

In the embodiment disclosed, there is a single outlet conduit 23 in the form of a pipe for transporting separated heavy phase from the separation space 17. This conduit 23 extends from a radially outer position of the separation space 17 to the heavy phase outlet 22. The conduit 23 has a conduit inlet 23a arranged at the radially outer position and a conduit outlet 23b arranged at a radially inner position. Further the outlet conduit 23 is arranged with an upward tilt relative to the radial plane from the conduit inlet 23a to the conduit outlet 23b. In other examples, the rotor casing may comprise at least two such outlet conduits 23, such as at least three, such as at least five, outlet conduits 23.

There is also a mechanically hermetically sealed inlet 20 for supply of the cell culture mixture to be processed to said separation space 17 via the distributor 24. The inlet 20 is in this embodiment connected to central duct 41 extending through the spindle 40, which thus takes the form of a hollow, tubular member. Introducing the cell culture mixture from the bottom provides a gentle acceleration of the cell culture. The spindle 40 is further connected to a stationary inlet pipe 7 at the bottom axial end of the separator 100 via a hermetic seal 15, such that the cell culture mixture to be separated may be transported to the central duct 41, e.g. by means of a pump. The separated liquid light phase is in this embodiment discharged via an outer annular duct 42 in said spindle 40. Consequently, the separated liquid phase of lower density is discharged via the bottom of the separator 100.

A first mechanical hermetic seal 15 is arranged at the bottom end to seal the hollow spindle 40 to the stationary inlet pipe 7. The hermetic seal 50 is an annular seal that surrounds the bottom end of the spindle 40 and the stationary pipe 7. The first hermetic seal 15 is a concentric double seal that seals both the inlet 21 to the stationary inlet pipe 7 and the liquid light phase outlet 21 to a stationary outlet pipe 9. There is also a second mechanical hermetic seal 16 that seals the heavy phase outlet 22 at the top of the separator 100 to a stationary outlet pipe 8.

As seen in FIG. 4, the inlet 20, and the cell phase outlet 22, as well as the stationary outlet pipe 8 for discharging separated cell phase, are all arranged around the rotational axis (X) so that cell culture mixture to be separated enters said rotor casing 2 at the rotational axis (X), as indicated by arrow "A", and the separated cell phase is discharged at the rotational axis (X), as indicated by arrow "B". The discharged liquid light phase is discharged at the bottom end of the centrifugal separator 100, as illustrated by arrow "C".

The centrifugal separator 100 is further provided with a drive motor 34. This motor 34 may for example comprise a stationary element and a rotatable element, which rotatable element surrounds and is connected to the spindle 40 such that it transmits driving torque to the spindle 40 and hence to the rotor casing 2 during operation. The drive motor 34 may be an electric motor. Furthermore, the drive motor 34 may be connected to the spindle 40 by transmission means. The transmission means may be in the form of a worm gear which comprises a pinion and an element connected to the spindle 40 in order to receive driving torque. The transmission means may alternatively take the form of a propeller shaft, drive belts or the like, and the drive motor 34 may alternatively be connected directly to the spindle 40.

During operation of the separator in FIG. 4, rotatable member 1 and thus rotor casing 2 are caused to rotate by torque transmitted from the drive motor 34 to the spindle 40. Via the central duct 41 of the spindle 40, cell culture mixture to be separated is brought into the separation space 17 via inlet 20. The inlet 20 and the stack 19 of separation discs are arranged so that the cell culture mixture enters the separation space 19 at a radial position that is at, to, or radially outside, the outer radius of the stack 19 of separation discs.

However, the distributor 24 may also be arranged to supply the liquid or fluid to be separated to the separation space at a radial position that is within the stack of separation discs, e.g. by axial distribution openings in the distributor and/or the stack of separation discs. Such openings may form axial distribution channels within the stack.

In the mechanically hermetic type of inlet 20, the acceleration of the liquid material is initiated at a small radius and is gradually increased while the liquid leaves the inlet and enters the separation space 17. The separation space 17 is intended to be completely filled with liquid during operation. In principle, this means that preferably no air or free liquid surfaces is meant to be present within the rotor casing 2. However, cell culture mixture may be introduced when the rotor is already running at its operational speed or at standstill. Cell culture mixture may thus be continuously introduced into the rotor casing 2.

Due to a density difference, the cell culture mixture is separated into a liquid light phase and a cell phase of higher density. This separation is facilitated by the interspaces between the separation discs of the stack 19 fitted in the separation space 17. The separated cell phase is collected from the periphery of the separation space 17 by conduit 23 and forced out through outlet 22 arranged at the rotational axis (X), whereas separated liquid light phase is forced radially inwards through the stack 19 and then led out through the annular outer duct 42 in the spindle 40.

FIG. 6 illustrates a method 50 according to embodiments. In the following reference is also made to FIGS. 1-5.

The method is a method 50 for separating a cell culture mixture comprising steps of:
 a) providing a centrifugal separator 100 according to any one of aspects and/or embodiments discussed herein, such as a centrifugal separator discussed above with reference to FIGS. 1-4;
 b) supplying said cell culture mixture to be separated to said inlet 20; and
 c) discharging a separated cell phase via said second mechanically hermetically sealed liquid outlet (22) and a liquid phase via said first mechanically hermetically sealed liquid outlet (21).

As an example, the cell culture mixture may comprise shear sensitive cells. Since the cell culture mixture is supplied into the rotor casing at the rotational axis (X) and since the separated cell phase is discharged at the rotational axis (X), the shear sensitive cells are introduced into, and discharged from, the rotor casing in a gentle manner.

The shear sensitive cells may be selected from Chinese hamster ovary (CHO) cells and mammalian cells.

In the method 50 it is understood that there is performed a step of: d) separating the cell culture mixture in the centrifugal separator 100.

According to embodiments of the method 50, the step b) may comprise a step of:
 e) supplying the cell culture mixture from an axially lower portion 200a of a fermenter tank 200 to the inlet 20 at an axially lower end of the centrifugal separator 100.

The axially lower end of the centrifugal separator may comprise the first axial end 5 of the rotor casing 2.

According to embodiments, the method 50 may comprise a further step of:
 f) discharging the separated cell phase to a tank 203 for re-use in a subsequent fermentation process. Since the separated cell phase is discharged at the rotational axis (X), the separated cell phase is discharged from the rotor casing in a gentle manner. Accordingly, the separated cell phase may be suitable for re-use in a subsequent fermentation process.

FIG. 5 is a schematic illustration of a system 300 for separating a cell culture mixture. The method 50 discussed herein may be performed in the system 300. The system comprises a fermenter tank 200 which is arranged to contain a cell culture mixture. The fermenter tank 200 has an axially upper portion and an axially lower portion 200a. The fermentation may for example be for expression of an extracellular biomolecule, such as an antibody, from a mammalian cell culture mixture. After fermentation, the cell culture mixture is separated in a centrifugal separator 100 according to the present disclosure. As seen in FIG. 5, the bottom of the fermenter tank 200 is connected via a connection 201 to the bottom of the separator 100, which may thus decrease the footprint and the complexity of the system 300. The connection 201 may be a direct connection or a connection via any other processing equipment, such as a tank. Thus, the connection 201 allows for supply of the cell culture mixture from the axially lower portion 200a of the fermenter tank 200 to the inlet at the axially lower end of the centrifugal separator 100, as indicated by arrow "A". After separation, the separated cell phase of higher density is discharged at the top of the separator, as indicated by arrow "B", whereas the separated liquid light phase of lower density, comprising the expressed biomolecule, is discharged via the liquid light phase outlet at the bottom of the separator 100, as indicated by arrow "C". The separated cell phase may be discharged to a tank 203 for re-use in a subsequent fermentation process, e.g. in the fermenter tank 200. The separated cell phase may further be recirculated to the feed inlet of the separator 100, as indicated by connection 202. The separated liquid light phase may be discharged to further process equipment for subsequent purification of the expressed biomolecule.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method for separating a cell culture mixture comprising the steps of:
   (a) providing a centrifugal separator comprising:
   a stationary frame;
   a rotatable assembly; and a drive unit for rotating the rotatable assembly relative the frame around an axis of rotation,
   wherein the rotatable assembly comprises a rotor casing enclosing a separation space in which a stack of separation discs is arranged to rotate around a vertical axis of rotation, said rotor casing further comprising:
   an inlet for supply of said cell culture mixture to said separation space;
   a first outlet for discharge of a separated liquid phase and a second outlet for discharge of a separated cell phase, said cell phase having a density that is higher than said liquid phase,
   wherein said inlet is arranged at a first axial end of said rotor casing and arranged so that the cell culture mixture to be separated enters said rotor casing at the rotational axis, and
   wherein said second outlet is arranged at a second axial end of said rotor casing opposite said first axial end and arranged so that said separated cell phase is discharged at the rotational axis;
   (b) supplying said cell culture mixture to be separated to said inlet; and
   (c) discharging the cell phase via said second outlet and the liquid phase via said first outlet.

2. The method according to claim 1, wherein the cell culture mixture comprises shear sensitive cells.

3. The method according to claim 2, wherein the shear sensitive cells are selected from CHO cells and mammalian cells.

4. The method according to claim 1, further comprising a step of:
   e) supplying the cell culture mixture from an axially lower portion of a fermenter tank to the inlet.

5. The method according to claim 1, comprising a further step of:
   f) discharging the separated cell phase to a tank for re-use in a subsequent fermentation process.

6. The method according to claim 1, wherein the outlets are free of any means for adding pressure for discharging the separated liquid phase and the separated cell phase.

7. The method according to claim 1, wherein the rotor casing further comprises at least one outlet conduit for transporting the separated cell phase from the separation space to the second outlet, said at least one outlet conduit extending from a radially outer position of said separation space to said second outlet.

8. The method according to claim 7, wherein said at least one outlet conduit comprises a conduit inlet arranged at the radially outer position and a conduit outlet at a radially inner position, and wherein the at least one outlet conduit is arranged with an upward tilt from the conduit inlet to the conduit outlet.

9. The method according to claim 1, wherein said at least one outlet conduit comprises a a first rotatable seal for sealing and connecting said inlet to a stationary inlet conduit, wherein at least a part of said stationary inlet conduit is arranged around rotational axis.

10. The method according to claim 1, further comprising a second rotatable seal for sealing and connecting said second outlet to a stationary outlet conduit arranged around rotational axis.

11. The method according to claim 1, wherein the rotatable assembly comprises an exchangeable separation insert and a rotatable member, said insert comprising said rotor casing and being supported by said rotatable member.

12. The method according to claim 11, wherein the outer surface of the exchangeable insert is engaged within a supporting surface of the rotatable member, thereby supporting said exchangeable insert within said rotatable member.

13. The method according to claim 1, wherein the rotatable assembly further comprises a spindle arranged to rotate coaxially with said rotor casing and wherein said spindle is rotatably supported by the stationary frame via at least one bearing.

14. The method according to claim 13, wherein said spindle comprises a central duct arranged around the axis of rotation and in fluid connection with said inlet, and wherein a first rotatable seal seals and connects said central duct to a stationary conduit.

15. The method according to claim 1, wherein the stack of separation discs comprises frustoconical separation discs.

16. The method according to claim 2, wherein the step b) comprises a step of:
   e) supplying the cell culture mixture from an axially lower portion of a fermenter tank to the inlet.

17. The method according to claim 3, wherein the step b) comprises a step of:
   e) supplying the cell culture mixture from an axially lower portion of a fermenter tank to the inlet.

18. The method according to claim 2, comprising a further step of:
   f) discharging the separated cell phase to a tank for re-use in a subsequent fermentation process.

19. The method according to claim 3, comprising a further step of:
   f) discharging the separated cell phase to a tank for re-use in a subsequent fermentation process.

20. The method according to claim 4, comprising a further step of:
   f) discharging the separated cell phase to a tank for re-use in a subsequent fermentation process.

* * * * *